United States Patent
Coleman et al.

(10) Patent No.: US 8,395,005 B2
(45) Date of Patent: Mar. 12, 2013

(54) PRODUCTION OF 1-BUTENE AND PROPYLENE FROM ETHYLENE

(75) Inventors: Steven T. Coleman, Humble, TX (US);
Gary A. Sawyer, Media, PA (US);
Robert S. Bridges, Friendswood, TX (US)

(73) Assignees: Equistar Chemicals, LP, Houston, TX (US); Lyondell Chemical Technology, L.P., Houston, TX (US)

( * ) Notice: Subject to any disclaimer, the term of this patent is extended or adjusted under 35 U.S.C. 154(b) by 233 days.

(21) Appl. No.: 12/903,794

(22) Filed: Oct. 13, 2010

(65) Prior Publication Data

US 2012/0095275 A1    Apr. 19, 2012

(51) Int. Cl.
*C07C 6/04* (2006.01)
*C07C 5/25* (2006.01)
*C07C 2/06* (2006.01)

(52) U.S. Cl. ........ 585/324; 585/326; 585/329; 585/643; 585/646; 585/510; 585/664

(58) Field of Classification Search .................. 585/324, 585/329, 326, 646, 510, 643, 664
See application file for complete search history.

(56) References Cited

U.S. PATENT DOCUMENTS

| | | |
|---|---|---|
| 3,321,546 A | 5/1967 | Roest et al. |
| 3,326,866 A | 6/1967 | Haag |
| 4,242,531 A | 12/1980 | Carter |
| 4,476,341 A | 10/1984 | Mathys |
| 4,575,575 A | 3/1986 | Drake |
| 4,992,612 A | 2/1991 | Suzukamo |
| 4,992,613 A | 2/1991 | Brownscombe |
| 5,120,894 A | 6/1992 | McCauley |
| 5,153,165 A | 10/1992 | Lowery |
| 5,260,499 A | 11/1993 | Wu |
| 5,300,718 A | 4/1994 | McCaulley |
| 5,414,178 A | 5/1995 | Wu |
| 6,586,649 B1 | 7/2003 | Botha et al. |
| 6,683,019 B2 | 1/2004 | Gartside et al. |
| 6,884,917 B1 | 4/2005 | Coleman |
| 7,074,976 B2 | 7/2006 | Powers et al. |
| 2004/0249229 A1 | 12/2004 | Gee et al. |
| 2006/0084831 A1 | 4/2006 | Zhang |
| 2008/0154078 A1 | 6/2008 | Bozzano |

FOREIGN PATENT DOCUMENTS

EP    2196444 A1    6/2010

OTHER PUBLICATIONS

PCT International Search Report and Written Opinion, mailed Dec. 7, 2011, for PCT/US2011/056169, filed Oct. 13, 2011.

*Primary Examiner* — Thuan D Dang

(57) ABSTRACT

A process for producing propylene and 1-butene is disclosed. The process comprises dimerizing ethylene in the presence of a dimerization catalyst to produce a dimerization mixture comprising 1-butene and 2-butenes. The dimerization mixture is distilled to produce a 1-butene stream containing 1-butene and ethylene, a 2-butenes stream, and a heavy stream. The 2-butenes stream is reacted with ethylene in the presence of a metathesis catalyst to produce a metathesis mixture comprising propylene, ethylene, and 2-butenes. Propylene is separated from the metathesis mixture.

12 Claims, 1 Drawing Sheet

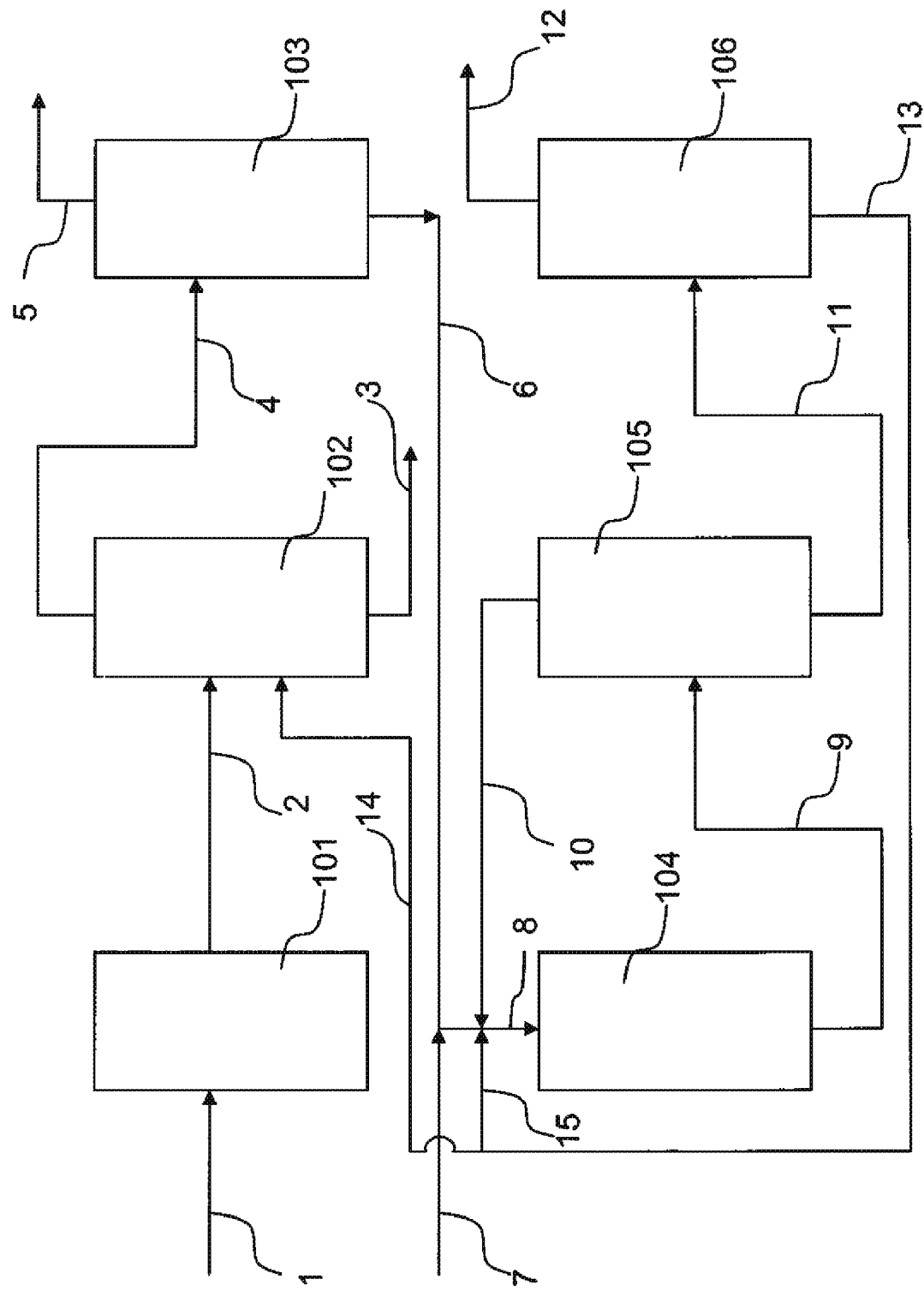

PRODUCTION OF 1-BUTENE AND PROPYLENE FROM ETHYLENE

FIELD OF THE INVENTION

The invention relates to a process for producing propylene and 1-butene from ethylene.

SUMMARY OF THE INVENTION

Steam cracking of hydrocarbon feedstocks produces ethylene, propylene, butenes (1-butene, isobutene, cis-2-butene, and trans-2-butene), butadiene, isoprene, aromatics, gasoline components, etc. Ethylene and propylene are important building blocks in the chemical industry. The relative proportions of ethylene and propylene produced in a steam cracking operation can be modulated to a certain extent by changing the nature of the feedstock and by modifying the operating conditions of the cracking to meet the market need. However, sometimes the market needs cannot be met by such modulation.

Metathesis reaction offers an opportunity to convert surplus olefins to other desirable olefins. For example, 2-butenes (cis-2-butene and trans-2-butene) can react with ethylene in the presence of a metathesis catalyst to produce propylene (U.S. Pat. Nos. 4,575,575, 5,120,894, 5,300,718, 6,586,649, 6,683,019, and 7,074,976). In one example, a mixture of 1-butene and 2-butenes obtained from a steam cracking process is reacted with ethylene to produce propylene. The process also generates heavier olefins such as pentenes and hexenes, which are useful gasoline blending components. In another example, ethylene is dimerized to form a dimerization mixture containing 1-butene and 2-butenes, which reacts with ethylene in a metathesis reaction to produce propylene. In this process, the 1-butene present in the dimerization mixture may react with 2-butene to form 2-pentene. 1-Butene can also form 3-hexene through metathesis.

It is desirable to reduce the amount of gasoline components formed and improve the yield of propylene from such processes.

SUMMARY OF THE INVENTION

This invention is a process for producing propylene and 1-butene. The process comprises dimerizing ethylene in the presence of a dimerization catalyst to produce a dimerization mixture comprising 1-butene and 2-butenes (cis-2-butene and trans-2-butene). The dimerization mixture is distilled to produce a 1-butene stream containing 1-butene and unreacted ethylene, a 2-butenes stream, and a heavy stream. The 2-butenes stream is reacted with ethylene in the presence of a metathesis catalyst to produce a metathesis mixture comprising propylene, ethylene, and 2-butenes. Propylene is separated from the metathesis mixture.

BRIEF DESCRIPTION OF THE DRAWING

FIG. 1 is a process flow diagram of one embodiment of the invention.

DETAILED DESCRIPTION OF THE INVENTION

The process of the invention comprises: (a) dimerizing ethylene in the presence of a dimerization catalyst to produce a dimerization mixture comprising ethylene, 1-butene, and 2-butenes; (b) distilling the dimerization mixture to produce a 1-butene stream comprising ethylene and 1-butene, a 2-butenes stream, and a heavy stream; (c) reacting the 2-butenes stream with ethylene in the presence of a metathesis catalyst to produce a metathesis mixture comprising propylene, ethylene, and 2-butenes; and (d) separating propylene from the metathesis reaction mixture.

The ethylene preferably has a purity of at least 99 wt %, more preferably at least 99.5 wt %, most preferably at least 99.9 wt %.

The dimerization catalyst can be a homogeneous catalyst or a heterogeneous catalyst. Examples of suitable homogeneous catalysts are taught in U.S. Pat. Nos. 3,321,546, 4,242,531, 4,476,341, 5,260,499 and 5,414,178, teachings of which on suitable dimerization catalysts are herein incorporated by reference. One such catalyst comprises a nickel compound and an organo aluminium compound. Suitable nickel compounds include nickel salts of a mono- or dicarboxylic acid, preferably an acid having from 5 to 20 carbon atoms, such as nickel oleate, nickel dodecanoate, and nickel octanoate. Other nickel compounds include coordination complexes of organic phosphines with nickel salts. Examples of such complexes are nickel bis(triethylphosphine) chloride [$Ni(Et_3P)_2Cl_2$], nickel bis(triphenylphosphine) octanoate, nickel bis(triphenylphosphine) chloride, and nickel bis(tricyclohexylphosphine) chloride. Suitable organo aluminium compounds include those having 1 to 2 alkyl groups and 1 to 2 halogen atoms per aluminium atom. The alkyl groups preferably have 1 to 5 carbon atoms. The halogen is preferably chlorine. One particularly preferred dimerization catalyst comprises nickel bis(triphenylphosphine) octanoate and ethyl aluminium dichloride. The molar ratio Ni:Al is generally from 0.9:1 to 1:0.9.

The dimerization reaction is typically performed at a temperature within a range of 10 to 100° C., preferably 20 to 80° C. The dimerization reaction can be carried out in a liquid or gas phase by contacting ethylene with the catalyst, depending on the reaction temperature and pressure employed. The pressure of the dimerization reaction is generally from 50 to 2,000 psig, preferably from 100 to 1,500 psig.

The dimerization reaction produces a dimerization mixture that comprises ethylene, 1-butene, and 2-butenes. Other olefins such as hexenes and octenes may is be present in the dimerization mixture. It is preferable to minimize the amount of hexenes, octenes, and other higher olefins produced. Generally, this can be achieved by selecting the appropriate catalyst and controlling ethylene conversion. Higher butenes selectivities can be achieved by running at lower ethylene conversions.

The process comprises distilling the dimerization mixture to produce a 1-butene stream, a 2-butenes stream, and a heavy stream. Such separation may be carried out by a single column distillation. The 1-butene stream is collected as an overhead fraction, which comprises unreacted ethylene and 1-butene. The heavy stream is collected as a bottoms fraction. The 2-butenes stream is obtained as a side draw. The distillations may take place in an apparatus suitable for this purpose, e.g., a bubble cap tray column, a column containing random packing, a column containing ordered packing, or a dividing wall column.

The distillation of the dimerization mixture can also be conveniently carried out with two distillation columns. In a first column, light components including ethylene, 1-butene, and 2-butenes are separated as overhead and the heavy components including hexenes, octenes are recovered from the bottom of the first distillation column. The light components are further distilled in a second column to separate the 1-butene stream (a mixture of 1-ethylene and 1-butene) from a 2-butenes stream. The first distillation column usually has from 10 to 50 theoretical plates, preferably from 12 to 25 theoretical plates. The distillation is typically carried out at a temperature of 20 to 130° C. and a pressure of 60 to 100 psig. The second distillation column preferably has from 60 to 200 theoretical plates, preferably from 100 to 170 theoretical plates. The distillation is typically carried out at a temperature of 20 to 100° C. and a pressure of 60 to 100 psig.

The 1-butene stream typically contains from 80 to 98 wt % 1-butene and from 2 to 20 wt % ethylene. This stream is suitable for preparing ethylene-1-butene polymers without further purification. The 2-butenes stream generally contains greater than 99 wt % 2-butenes, preferably greater than 99.5 wt % 2-butenes.

The 2-butenes stream is reacted with ethylene in the presence of a metathesis catalyst to form a metathesis mixture comprising ethylene, propylene, and 2-butenes. Metathesis catalysts are well known in the art (U.S. Pat. Nos. 4,575,575, 5,120,894, 5,300,718, 6,586,649, 6,683,019, and 7,074,976). Typically, the metathesis catalyst comprises a transition metal oxide. Suitable transition metal oxides include oxides of cobalt, molybdenum, rhenium, tungsten, and mixtures thereof. Generally the catalyst is supported on a carrier. Suitable carriers include silica, alumina, titania, zirconia, zeolites, clays, and mixtures thereof. Silica and alumina are preferred. The catalyst may be supported on a carrier in any convenient fashion, particularly by adsorption, ion-exchange, impregnation, or sublimation. The transition metal oxide constituent of the catalyst may amount to 1 to 30 wt % of the total catalyst, preferably 5 to 20 wt %.

One preferred metathesis catalyst comprises tungsten oxide supported on a silica carrier. Preferred silica carriers are high purity silicas, i.e., have very low levels of sodium (e.g., less than 2000 ppm $Na_2O$) and aluminum (e.g., less than 2000 ppm $Al_2O_3$). Generally, the silica carrier has a surface area of at least 10 square meters per gram. Preferably, the surface area is at least 50 square meters per gram.

To prepare a tungsten oxide-on-silica catalyst, an aqueous solution or suspension of tungsten oxide or a tungsten oxide precursor may be used to contact a silica carrier. Suitable tungsten oxide precursors are compounds that are convertible to the oxide form under calcination conditions, such as, for example, halides, sulfides, sulfates, nitrates, carboxylates, and the like, and mixtures thereof. Exemplary tungsten compounds include tungsten pentabromide, tungsten dichloride, tungsten tetrachloride, tungsten hexafluoride, tungsten trioxide, tungsten dioxydichloride, tungsten trisulfide, metatungstic acid, orthotungstic acid, ammonium phosphotungstate, ammonium metatungstate, and mixtures thereof.

The metathesis catalyst may be a powder or particulates. Particulate catalysts are preferred. Suitable catalysts includes beads, granules, pellets, extrudates, tablets, agglomerates, honeycomb monolith, and the like, generally having a particle size of greater than 1 mm.

The tungsten oxide-on-silica catalyst is preferably used in a fixed-bed reactor. The metathesis reaction is generally performed at a temperature of 200 to 500° C., preferably at 250 to 400° C., and under a pressure of 50 to 450 psig. The weight hourly space velocities are typically from 0.2 to 4 kg feed per kg catalyst per hour.

The metathesis mixture comprises ethylene, propylene, and 2-butenes. Ethylene and propylene can be separated from the 2-butenes in separate steps by standard techniques (U.S. Pat. No. 6,884,917). Preferably the propylene has a purity of at least 99 wt %, more preferably at least 99.5 wt %. The ethylene and 2-butenes separated from the metathesis mixture may be recycled to the metathesis reaction.

If desirable, a portion of the 2-butenes stream separated from the dimerization mixture or from the metathesis mixture may be isomerized to produce an isomerization mixture comprising 1-butene and 2-butenes, so that additional 1-butene can be separated from the isomerization mixture. The amount of 2-butenes isomerized depends on the market need for propylene relative to 1-butene.

In an isomerization reaction, 2-butenes is contacted with an isomerization catalyst to produce an isomerized stream. At least a portion of 2-butenes in the feed stream is converted to 1-butene by the isomerization. The amount of 1-butene formed depends on the catalyst used and the reaction conditions. The molar ratio of 1-butene to 2-butenes in the isomerized stream is preferably in the range of 1:10 to 3:10.

Many isomerization catalysts can be used. Suitable acidic catalysts include acidic ion-exchange resins such as sulfonated resins (see, e.g., U.S. Pat. No. 3,326,866), organosulfonic acids, phosphoric acid, carboxylic acids, metal oxides (alumina, zirconia, sulfated zirconia), mixed oxides (e.g., silica-alumina, zirconia-silica), acidic zeolites, acidic clays (see, e.g., U.S. Pat. No. 4,992,613; U.S. Pat. Appl. Pub. Nos. 2004/0249229 and 2006/0084831).

When an acidic catalyst is used, the isomerization is typically conducted at a temperature from 40 to 200° C., preferably from 90 to 150° C., and under a pressure of 50 to 500 psig, preferably from 100 to 300 psig. The weight hourly space velocities (WHSV) are generally maintained at 0.2 to 4 kg feed per kg catalyst per hour.

The basic isomerization catalysts are preferably metal oxides such as magnesium oxide, calcium oxide, barium oxide, and lithium oxide. Metal oxides supported on a carrier may be used. Suitable carriers include silica, alumina, titania, silica/alumina, and the like, and mixtures thereof (see, e.g., U.S. Pat. Nos. 5,153,165, 5,300,718, 5,120,894, and 4,992, 612). A particularly preferred basic isomerization catalyst is magnesium oxide. Suitable magnesium oxide has a surface area of at least 1 $m^2/g$, preferably >5 $m^2/g$. The magnesium oxide is to preferably activated in a suitable manner, for example, by heating in a flowing stream of an oxygen-containing gas for about 1 to about 30 h at 250 to 800° C., preferably at 300 to 600° C. before use.

The isomerization reaction in the presence of magnesium oxide catalyst may be conducted at a temperature ranging from 50 to 500° C., preferably ranging from 150 to 450° C., most preferably ranging from 250 to 300° C., and at a pressure and a residence time effective to give a desired composition of the isomerized stream.

The isomerization catalysts are preferably beads, granules, pellets, extrudates, tablets, agglomerates, and the like. The catalyst is preferably used in a fixed bed and the reaction is performed in a continuous flow mode.

EXAMPLE

A method for practicing the invention is shown in FIG. 1. Ethylene, along with a catalyst (nickel bis(triphenylphosphine) octanoate, 0.006 kg/min, and ethyl aluminum dichloride, 0.004 kg/min, is fed to a dimerization loop reactor 101 via line 1. The loop reactor is described in U.S. Pat. No. 4,242,531. A solution of the catalyst in hexanes may be used. The dimerization reactor is operated at a pressure of 200 psig and a temperature of from 40 to 65° C.

The reaction mixture exits reactor 101 and is contacted with a dilute (5%) caustic solution, then washed with water (not shown). The washed dimerization mixture enters butenes fractionation column 102 via line 2. Column 102 has 13 theoretical plates and is operated under a pressure of 78 psig and at a temperature of 125° C. at the bottom of the column and at 49° C. at the top of the column. Light components including ethylene, 1-butene, and 2-butenes are separated as an overhead in line 4 and a heavy fraction containing hexenes and $C_{7}+$ olefins is recovered from the bottom and exits column 102 via line 3. The heavy fraction is useful as gasoline blending components.

The light fraction from column 102 enters column 103 via line 4 and is separated into a 1-butene stream in line 5 (a mixture of ethylene and 1-butene) and a 2-butenes stream in line 6. Column 103 has 150 theoretical plates and is operated under a pressure of 72 psig and at a temperature of 62° C. at the bottom and at 49° C. at the top of the column.

The 2-butenes stream in line 6 is mixed with fresh ethylene from line 7, recycled 2-butenes in line 15, and recycled ethylene in line 10 and fed to metathesis reactor 104 via line 8. Reactor 104 contains a tungsten oxide-on-silica catalyst and is operated at 330° C. and 500 psig. A metathesis mixture exits reactor 104 via line 9, is cooled to 15° C., and enters deethenizer 105. Deethenizer 105 has 40 theoretical plates and is operated at a pressure of 400 psig and at a temperature of 95° C. at the bottom and at 0° C. at the top of the column. Ethylene is recovered as an overhead and recycled to reactor 104 via line 10. The bottoms stream from deethenizer 105 is fed to propylene tower 106 via line 11. Propylene tower 106 has 45 theoretical plates and is operated at a pressure of 355 psig and at a temperature of 130° C. at the bottom and at 49° C. at the top of the column. Polymer grade propylene (99.5% pure) is recovered as overhead in line 12. The bottoms stream containing unreacted 2-butenes exits the tower 106 via line 13. Majority of the flow in line 13 (95%) is recycled to metathesis reactor 104 via line 15. The rest (5%) is fed to column 102 via line 14 as a heavy purge.

The expected flow rates of various components in the streams are shown in Table 1.

We claim:

1. A process for producing propylene and 1-butene from ethylene comprising:
   (a) dimerizing ethylene in the presence of a dimerization catalyst to produce an dimerization mixture comprising ethylene, 1-butene, and 2-butenes;
   (b) distilling the dimerization mixture to produce a 1-butene stream comprising ethylene and 1-butene, a 2-butenes stream, and a heavy stream, wherein the 1-butene stream contains from 80 to 98 wt. % 1-butene and from 2 to 20 wt. % ethylene and the 2-butenes stream contains greater than 99 wt. % 2-butenes;
   (c) reacting the 2-butenes stream with ethylene in the presence of a metathesis catalyst to produce a metathesis mixture comprising propylene, ethylene, and 2-butenes; and
   (d) separating propylene from the metathesis reaction mixture.

2. The process of claim 1 further comprising isomerizing the 2-butenes stream to produce an isomerization mixture comprising 1-butene and 2-butenes in the presence of an isomerization catalyst.

3. The process of claim 2 wherein the isomerization mixture is further processed in step (b).

4. The process of claim 2 wherein the isomerization catalyst comprises magnesium oxide.

5. The process of claim 1 further comprising separating ethylene from the metathesis mixture and recycling the separated ethylene to step (c).

6. The process of claim 1 further comprising separating 2-butenes from the metathesis mixture and recycling the separated 2-butenes to step (c).

7. The process of claim 1 wherein the ethylene has a purity of at least 99.9 wt %.

8. The process of claim 1 wherein the dimerization catalyst comprises a nickel compound and an organoaluminum compound.

9. The process of claim 1 wherein the dimerization catalyst comprises nickel bis(triphenylphosphine) octanoate and ethyl aluminium dichloride.

10. The process of claim 1 wherein the propylene obtained from step (d) has a purity of at least 99.5 wt %.

11. The process of claim 1 wherein the metathesis catalyst comprises tungsten oxide.

12. The process of claim 1 wherein the metathesis catalyst comprises tungsten oxide and silica.

TABLE 1

Flow Rates of Various Components (Kg/h)

| Stream | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Ethylene | 500.00 | 5.00 | | 5.00 | 5.00 | | 197.77 | 532.82 | 336.53 | 335.04 | 1.48 | 1.48 | | |
| Propylene | | | | 0.15 | 0.15 | | | 6.29 | 595.06 | 3.35 | 591.70 | 588.61 | 3.09 | 0.15 |
| 1-Butene | | 30.00 | 0.15 | 30.09 | 29.79 | 0.30 | | 4.92 | 4.87 | | 4.87 | | 4.87 | 0.24 |
| Cis-2-Butene | | 125.00 | 1.92 | 125.91 | 0.01 | 125.90 | | 179.68 | 58.08 | | 58.08 | 1.48 | 56.60 | 2.83 |
| Trans-2-Butene | | 275.00 | 4.18 | 274.69 | 0.02 | 274.67 | | 348.22 | 77.42 | | 77.42 | | 77.42 | 3.87 |
| 1-Pentene | | | 0.33 | 0.02 | | 0.02 | | 6.54 | 6.86 | | 6.86 | | 6.86 | 0.34 |
| Cis-2-Pentene | | | 0.02 | | | | | 0.49 | 0.51 | | 0.51 | | 0.51 | 0.03 |
| Trans-2-Pentene | | | 0.05 | | | | | 1.04 | 1.10 | | 1.10 | | 1.10 | 0.05 |
| 1-Hexene | | | | | | | | 0.00 | 0.00 | | 0.00 | | 0.00 | 0.00 |
| Cis-2-Hexene | | | 0.11 | | | | | 2.20 | 2.32 | | 2.32 | | 2.32 | 0.12 |
| Trans-2-Hexene | | 60.00 | 59.48 | 0.60 | | 0.60 | | 2.23 | 1.71 | | 1.71 | | 1.71 | 0.09 |
| Cis-3-Hexene | | | | | | | | | | | | | | |
| Trans-3-Hexene | | | | | | | | | | | | | | |
| C7+ | | 5.00 | 5.00 | | | | | 0.03 | 0.03 | | 0.03 | | 0.03 | |
| Total | 500.00 | 500.00 | 71.26 | 436.47 | 34.98 | 401.49 | 197.77 | 1084.46 | 1084.49 | 338.40 | 746.09 | 591.57 | 154.52 | 7.73 |

* * * * *